United States Patent
Takahashi

(10) Patent No.: US 9,311,695 B2
(45) Date of Patent: Apr. 12, 2016

(54) IMAGE PROCESSING METHOD AND RADIOGRAPHIC APPARATUS USING THE SAME

(75) Inventor: Wataru Takahashi, Uji (JP)

(73) Assignee: SHIMADZU CORPORATION, Kyoto (JP)

( * ) Notice: Subject to any disclaimer, the term of this patent is extended or adjusted under 35 U.S.C. 154(b) by 1243 days.

(21) Appl. No.: 13/069,604

(22) Filed: Mar. 23, 2011

(65) Prior Publication Data

US 2011/0235888 A1  Sep. 29, 2011

(30) Foreign Application Priority Data

Mar. 26, 2010  (JP) ................................. 2010-072205

(51) Int. Cl.
*G06T 5/00* (2006.01)
*A61B 6/00* (2006.01)

(52) U.S. Cl.
CPC ............... *G06T 5/002* (2013.01); *A61B 6/5205* (2013.01); *G06T 5/009* (2013.01); *G06T 2207/10116* (2013.01); *G06T 2207/20016* (2013.01); *G06T 2207/20192* (2013.01)

(58) Field of Classification Search
CPC .................... A61B 6/5258; G06T 2207/20182; G06T 2207/201829
See application file for complete search history.

(56) References Cited

U.S. PATENT DOCUMENTS

| | | | |
|---|---|---|---|
| 5,602,599 A * | 2/1997 | Greggain | 348/581 |
| 5,949,915 A | 9/1999 | Yamada | |
| 6,072,913 A | 6/2000 | Yamada | |
| 6,728,381 B1 | 4/2004 | Hosoya | |
| 6,813,389 B1 * | 11/2004 | Gindele et al. | 382/274 |
| 6,826,295 B2 * | 11/2004 | Lichtermann et al. | 382/124 |
| 2002/0006230 A1 * | 1/2002 | Enomoto | 382/261 |
| 2003/0160800 A1 * | 8/2003 | Vuylsteke | G06T 5/009 345/589 |
| 2004/0042679 A1 * | 3/2004 | Yamada | 382/260 |
| 2008/0137925 A1 * | 6/2008 | Bertens | G06K 9/527 382/128 |
| 2008/0260232 A1 * | 10/2008 | Ohara et al. | 382/132 |
| 2009/0285461 A1 * | 11/2009 | Bohm | G06K 9/40 382/128 |

(Continued)

FOREIGN PATENT DOCUMENTS

| | | | |
|---|---|---|---|
| JP | 9-163227 A | 6/1997 | |
| JP | 10-63837 A | 3/1998 | |
| JP | 10-75364 A | 3/1998 | |
| JP | 10-75395 A | 3/1998 | |

(Continued)

OTHER PUBLICATIONS

Notification of Reasons for Refusal for the Application No. 2010-072205 from Japan Patent Office mailed Feb. 12, 2013.

*Primary Examiner* — Kim Vu
*Assistant Examiner* — Nathan Bloom
(74) *Attorney, Agent, or Firm* — Cheng Law Group, PLLC

(57) ABSTRACT

An image processing method is provided including the steps of generating a first band image through high-pass filter processing to a source image having an image of a subject falling thereon; generating a reduction image through reduction of the source image; performing low-pass filter processing to the reduction image to generate a low-pass image; magnifying the low-pass image to generate a magnified low-pass image; generating a second band image based on the source image, the first band image, and the magnified low-pass image; generating a third band image through performing of band-pass filter processing to the reduction image; and performing image processing to the source image with each of the band images.

16 Claims, 9 Drawing Sheets

(56) References Cited

U.S. PATENT DOCUMENTS

| | | | |
|---|---|---|---|
| 2010/0195886 A1* | 8/2010 | Bertens | G06T 7/2066 382/131 |
| 2010/0290714 A1 | 11/2010 | Toyoda et al. | |
| 2010/0322509 A1* | 12/2010 | Shimizu et al. | 382/162 |
| 2011/0280463 A1* | 11/2011 | Takahashi | A61B 6/5205 382/132 |

FOREIGN PATENT DOCUMENTS

| | | |
|---|---|---|
| JP | 10-633838 A | 3/1998 |
| JP | 10-171983 A | 6/1998 |
| JP | 10-191260 A | 7/1998 |
| JP | 2008-212524 A | 9/2008 |
| WO | WO-2009/107197 A1 | 9/2009 |

* cited by examiner

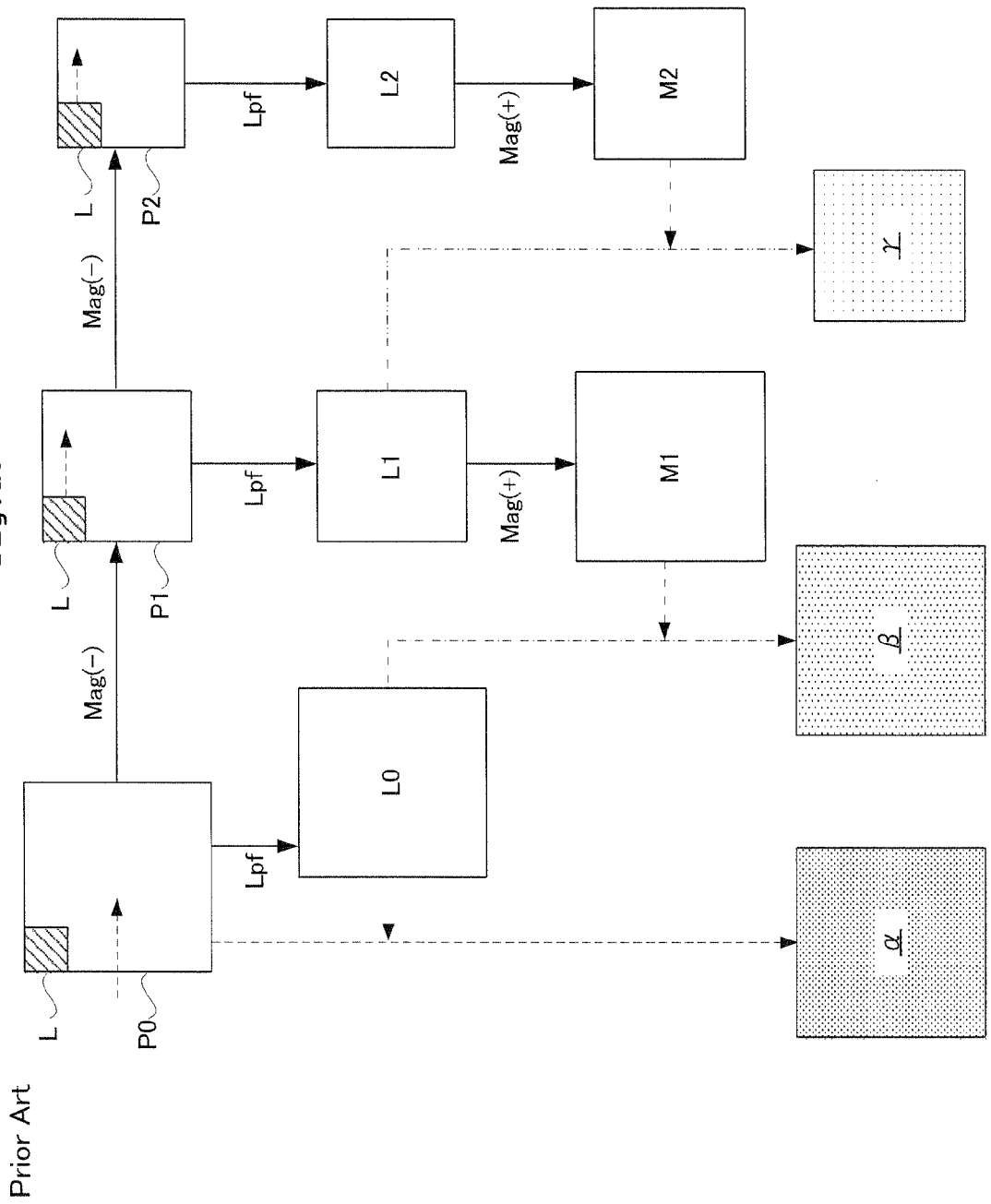

IMAGE PROCESSING METHOD AND RADIOGRAPHIC APPARATUS USING THE SAME

BACKGROUND OF THE INVENTION (1) Field of the Invention

This invention relates to a method of image-processing a radiographic image with a subject falling thereon, and radiographic apparatus using thereof. More particularly, this invention relates to an image-processing method that allows noise reduction processing, high frequency enhancement processing, and dynamic range compression processing, and radiographic apparatus using the method.

(2) Description of the Related Art

Medical institutions are equipped with radiographic apparatus for acquiring an image of a subject with radiation. When an image is subject to given image processing, the image has a noise removed therefrom or a structure of such as a blood vessel emphasized that falls thereon, which may result in easier diagnosis. Accordingly, the conventional radiographic apparatus may process an acquired image through image processing. Specifically, examples of the image processing in which the radiation photography apparatus may adopt include noise reduction processing, high frequency enhancement processing, and dynamic range compression processing. See Japanese Patent Publications No. H10-171983, H10-75364, H10-75395, H9-163227, H10-63837, and H10-63838.

In order to perform the above three image processing, two or more band images need to be generated from a radiographic image appearing a subject (hereinafter, appropriately referred to as a source image.) Here, the band image is an image formed of only frequency components in a certain band in the source image. A given frequency component is extracted from the source image through application of a band-pass filter for passing the frequency components of the band in the source image. Two or more band images are generated based on the source image. They differ from one another in band with the frequency components extracted from the source image. Consequently, one band image contains only high frequency components in the source image, whereas another band image contains only low frequency components in the source image. The band images are sequentially generated from a high frequency component side through image processing to the source image. Here, the high frequency component in the source image is a component with a detailed structure in a projected image of the subject falling thereon. The low frequency component in the source image is a component with a rough structure in the projected image of the subject falling thereon.

Now, description will be given of one method of generating a conventional band image. A first method uses a high-pass filter H and a band-pass filter B as illustrated in FIG. 18. According to the first method, the high-pass filter H is applied to the source image P0, as illustrated in FIG. 18(a). The high-pass filter H is an image filter specified by a matrix that extracts the high frequency components from the source image P0. FIG. 18 schematically illustrates the high-pass filter H applied to an upper left end of the source image P0, whereby high frequency components are extracted in the upper left end of the source image P0. This operation is shown by arrows in dotted lines. The high-pass filter H is applied to the source image P0 while moving with respect thereto, and the high frequency component is extracted throughout the source image P0, whereby a first band image α is generated having only the high frequency components falling thereon. The first band image α has the same size as the source image P0. In FIG. 18, image conversion processing using the high-pass filter H is expressed with a symbol Hpf.

Next, a band-pass filter B is applied to the source image P0, as illustrated in FIG. 18(b). The band-pass filter B is an image filter having a larger specified matrix than the high-pass filter H. FIG. 18 schematically illustrates the band-pass filter B applied on an upper left end of the source image P0, and thus a component is extracted within a higher frequency range in the upper left end of the source image P0. The frequency component extracted at this time has lower frequencies than the component extracted through the high-pass filter H. Consequently, with the bypass filter H, the frequency component is extracted from the source image P0 that is lower than that in the band of the first band image α. This operation is shown by arrows in dotted lines. The band-pass filter B is applied to the source image P0 while moving with respect thereto, and the high frequency components are extracted throughout the source image P0, whereby a second band image β is generated having only the components in the higher frequency range falling thereon. The second band image β has the same size as the source image P0. In FIG. 18, image conversion processing using the band-pass filter B is expressed by a symbol Bpf.

Thereafter, the source image P0 is reduced in size for generating a reduction image P1 (see FIG. 18(c).) The same operation as that in FIG. 18(b) is performed to the reduction image P1 for generating a third band image γ. Subsequently, the reduction image P1 is also reduced in size for generating a reduction image P2 (see FIG. 18(d).) The same operation as that in FIG. 18(b) is performed to the reduction image P2 for generating a fourth band image δ. In FIG. 18, the process for reducing an image is expressed by a symbol Mag(-).

In general, more components of the low frequencies in the source image are extracted as the matrix specifying the band-pass filter B increases in dimension with respect to the image. When the matrix specifying the band-pass filter B increases in dimension so as to extract the lower frequency components from the source image, parameters in the matrix increase, which leads to time-consuming for filtering. Here, the foregoing configuration reduces an image to be used for the image conversion processing instead of increasing in size the band-pass filter B upon extraction of the components of the low frequencies. Accordingly, it is not necessary to increase in dimension the matrix specifying the band-pass filter B, which results in high-speed image processing. As illustrated in FIG. 18, the images as a source of the band images β, δ, γ are small in this order. As a result, the band images β, δ, γ have components of the low frequency in this order in the source image P0. As noted above, the band images α, β, δ, γ are generated having the frequency components in various frequency bands extracted from the source image P0. The band images α, β, δ, γ have the extracted low frequency components in the source image P0 in this order, and are used for noise reduction processing, etc.

Description will be given of another method of generating a band image. A second method uses a low-pass filter L as illustrated in FIG. 19. According to the second method, the low-pass filter L is applied to the source image P0, as illustrated in FIG. 19. The low-pass filter L is an image filter specified by a matrix that may remove the high frequency components from the source image P0. FIG. 19 schematically illustrates the high-pass filter H applied on an upper left end of the source image P0, and removes the high frequency components in the upper left end of the source image P0. This operation is shown by arrows in dotted lines. The low-pass filter L is applied to the source image P0 while moving with respect thereto, and the high frequency components are removed throughout the source image P0, whereby a low-pass image L0 is generated having the high frequency components removed therefrom.

Next, description will be given of a method of generating the first band image α. In order to generate the first band image α, the low-pass image L0 is subtracted from the source image P0, as illustrated by a path in dashed lines in FIG. 19. Taking into consideration that the low-pass image L0 is an image having the high frequency components removed from the source image P0, the high frequency components contained in the source image P0 are outputted through the subtraction. This corresponds to the first band image α. The first band image α, the low-pass image L0, and the source image P0 all have the same size. In FIG. 19, image conversion processing using the low-pass filter L is expressed by a symbol Lpf.

Upon generation of the second band image β, the source image P0 is firstly reduced in size for generating the reduction image P1. The same operation as above is performed to the reduction image P1 for generating a low-pass image L1. The low-pass image L1 is magnified so as to have the same size as the low-pass image L0, whereby a magnified low-pass image M1 is generated. Thereafter, the magnified low-pass image M1 is subtracted from the low-pass image L0 as illustrated by a path in dashed lines in FIG. 19. The subtraction result is the second band image β. In FIG. 19, a process for reducing an image is expressed by a symbol Mag(−), and a process for magnifying an image by Mag(+).

Here, more components are removed having the lower frequencies than the source image as the matrix specifying the low-pass filter L increases in dimension with respect to the image. According to the second method, the matrix specifying the low-pass filter L increases in dimension with respect to the reduction image as the image with the low-pass filter L applied thereto is reduced. Reduction of the image may realize the same effect as that obtained through increasing in dimension of the matrix specifying the low-pass filter. In comparison of the low-pass image L0 and the magnified low-pass image M1, the magnified low-pass image M1 has more removed components of low frequencies.

The magnified low-pass image M1 is subtracted from the low-pass image L0, as illustrated by a path in dashed lines in FIG. 19, whereby the high frequency component in the low-pass image L0 is outputted. This corresponds to the second band image β. The second band image β, the low-pass image L0, and the magnified low-pass image M1 all have the same size.

Upon generation of the third band image γ, the reduction image P1 is firstly reduced in size for generating the reduction image P2. The same operation as above is performed to the reduction image P2 for generating a low-pass image L2. The low-pass image L2 is magnified so as to have the same size as the low-pass image L1, whereby a magnified low-pass image M2 is generated. Thereafter, the magnified low-pass image M2 is subtracted from the low-pass image L1, as shown by a path in dashed lines in FIG. 19, to acquire the third band image γ. The third band image γ, the low-pass image L1, and the magnified low-pass image M2 all have the same size. As noted above, the band images α, β, δ, γ are generated having the frequency components in various frequency bands extracted from the source image P0, and are used for noise reduction processing, etc.

However, the foregoing image processing method by the radiographic apparatus has following drawbacks.

According the first method, there arises a drawback of time-consuming generation of the band image. Upon generation of the band image, the low frequency components need to be extracted from the image. Consequently, filtering has to be performed using a matrix in a large dimension. The conversion process using the matrix with a large dimension needs increased pixel data for calculation, which leads to much time involved. Particularly, it takes most time for generating the second band image β. That is because the matrix in a larger dimension has to be applied throughout the source image P0 in a larger size. Such slow processing may be a problem particularly in real time processing to moving images.

In addition, according to the second method, there arises a problem that a false image may appear in the band image to be generated and an artifact may occur in the image generated through the noise reduction processing to the false image, etc. That is, the second method needs to have steps of further reducing the source image and further magnifying the low-pass image than in the first method for generating the band image. In general, when a reducing process is performed to generate a reduction image and a filter in an original size is applied to the reduction image instead of applying the magnified filter to an image, the low-pass image in the reduced image is to deteriorate than that in the source image. Moreover, further magnified processing may degrade the low-pass image in the reduced image than that in the source image.

The reason for the above will be described. The reduction image is an image obtained through bundling of pixels in the source image together for reduction. The reduction image corresponds to an image in which a box filter is applied to the source image for performing discrete sampling. Here, the number of pixels forming the reduction image is fewer than that of the source image. Consequently, even when the filter in the original size is applied to the reduced image, processing is not performed similarly to a case where the magnified filter is applied to the source image under an influence that the box filter is applied in advance. In addition, generation of the reduction image is irreversible image processing. Information on the source image having the defect reduction image cannot be recovered completely although it may be estimated through interpolation. Consequently, although the image is magnified, defect information due to the discrete sampling cannot be recovered completely, but image quality thereof may deteriorate. There is no other way not to reduce or magnify the image for preventing artifacts from occurring in the image. Accordingly, the low-pass filter L is to be applied to the source image P0 while the matrix increases in dimension. As a result, the band image with no artifact may be acquired, but on the other hand, it takes much time for generating the image.

This invention has been made regarding the state of the art noted above, and its object is to provide an image processing method that allows image processing at low calculation load while possibly suppressing artifacts occurring in the image processing, and radiographic apparatus using the method.

SUMMARY OF THE INVENTION

This invention is constituted as stated below to achieve the above object. An image processing method according to this invention includes a first band image generation step for generating a first band image through high-pass filter processing to a source image having an image of a subject falling thereon; a source image reduction step for generating a reduction image through reduction of the source image; a low-pass filter processing step for performing low-pass filter processing to the reduction image to generate a low-pass image; an image magnifying step for magnifying the low-pass image to generate a magnified low-pass image; a second band image generation step for generating a second band image based on the source image, the first band image, and the magnified low-pass image; a third band image generation step for generating a third band image through performing of band-pass filter processing to the reduction image; and an image processing step for performing image processing to the source image with each band image.

Moreover, radiographic apparatus according to this invention includes a radiation source for emitting radiation; a radiation detecting device for detecting radiation; an image generation device for generating a source image having an image of a subject falling thereon in accordance with a detection signal outputted from the radiation detecting device; a first band image generation device for generating a first band image through high-pass filter processing to the source image; a source image reduction device for generating a reduction image through reduction of the source image; a low-pass filter processing device for performing low-pass filter processing to the reduction image to generate a low-pass image; an image magnifying device for magnifying the low-pass image to generate an magnified low-pass image; a second band image generation device for generating a second band image based on the source image, the first band image, and the magnified low-pass image; a third band image generation device for generating a third band image through performing of band-pass filter processing to the reduction image; and an image-processing device for performing image processing to the source image with each band image.

According to the foregoing configuration, the source image is once reduced and the low-pass filter is applied thereto. Thereafter, it is magnified for generating the magnified low-pass image. The second band image is generated with the magnified low-pass image. Accordingly, the low-pass filter in a minimum dimension is applied to the image in a small size. Consequently, it does not need much time for generating the second band image. Moreover, according to the configuration of this invention, the band-pass filter is applied to the reduced image for acquiring the third band image. That is, the configuration of this invention has no configuration as adopted in the second method in the conventional art that performs redundant reduction/magnifying of the image. Accordingly, the third band image has a few artifacts. It takes most time for generating the second band image. Consequently, according to this invention, the second band image has to be generated at a high-speed for an enhanced processing speed for the band image generation. Giving attention to this, the method required for performing redundant reduction/magnifying of the image at a high speed is adopted only for generating the second band image. Accordingly, the image processing method and radiographic apparatus may be provided having balanced generating time and image quality of the band image.

Moreover, it is more desirable that the foregoing image processing method further includes a noise removal step for removing noise components superimposed in the source image through extraction of the noise components from each band image.

Furthermore, it is more desirable that the image-processing device in the foregoing radiographic apparatus removes noise components superimposed in the source image through extraction of the noise components from each band image.

The foregoing configuration is one example of specific configurations representing the image processing with each band image. Acquiring of the band image may realize estimation of the noise components superimposed in the source image, thereby positively removing the noise components from the source image.

Moreover, it is more desirable that the foregoing image processing method further includes a first combined image acquisition step for acquiring a first combined image containing the high frequency components in the source image through weighting to each band image and adding them up, and a high frequency enhancement processing step for performing high frequency enhancement processing to the source image by performing weighting to the combined image and the source image and adding them up.

Furthermore, it is more desirable that the image processing device in the foregoing radiographic apparatus acquires a combined image containing the high frequency components in the source image through weighting to each band image and adding it up, and performs high frequency enhancement processing to the source image by applying weighting to the combined image and the source image and adding them up.

The foregoing configuration is one example of specific configurations representing the image processing with each band image. Applying of weighting to each band image and adding thereof may realize acquiring of the combined image containing no low frequency component in the source image. When this, the source image, and the combined image are subject to weighting and addition, the high frequency component in the source image may be enhanced.

Moreover, it is more desirable that the foregoing image processing method further includes a low component frequency image acquisition step for acquiring the low frequency component image containing low frequency components in the source image; a second combined image acquisition step for acquiring a combined image containing high frequency components in the source image through weighting to each band image and adding them up; a reversal step for reversing pixel data nonlinearly that form the combined image and the low frequency component image, respectively, to generate a reverse image; and dynamic range compression processing step for performing dynamic range compression processing to the source image through weighting to the reverse image and the source image and adding them up.

It is more desirable that the image processing device in the foregoing radiographic apparatus acquires the low frequency component image containing the low frequency components in the source image; acquires a combined image containing high frequency components in the source image through weighting to each band image and adding it up; reverses pixel data nonlinearly that form the combined image and the low frequency component image, respectively, to generate a reverse image; and performs dynamic range compression processing to the source image through weighting to the reverse image and the source image and adding thereof.

The foregoing configuration is one example of specific configurations representing the image processing with each band image. Here, the low frequency component image containing the low frequency components in the source image may be acquired through adding up each band image and subtracting thereof from the source image. Moreover, the combined image containing the high frequency components in the source image may be acquired through weighting to each band image and adding it up. These images are prepared individually and the dynamic range compression processing is performed to the source image, whereby the dynamic range compression processing may be controlled per each component through control of the methods of generating the low frequency component image and the combined image.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

FIGS. 18 and 19 are schematic views each illustrating conventional X-ray apparatus.

DESCRIPTION OF THE PREFERRED EMBODIMENTS

Figure 1:
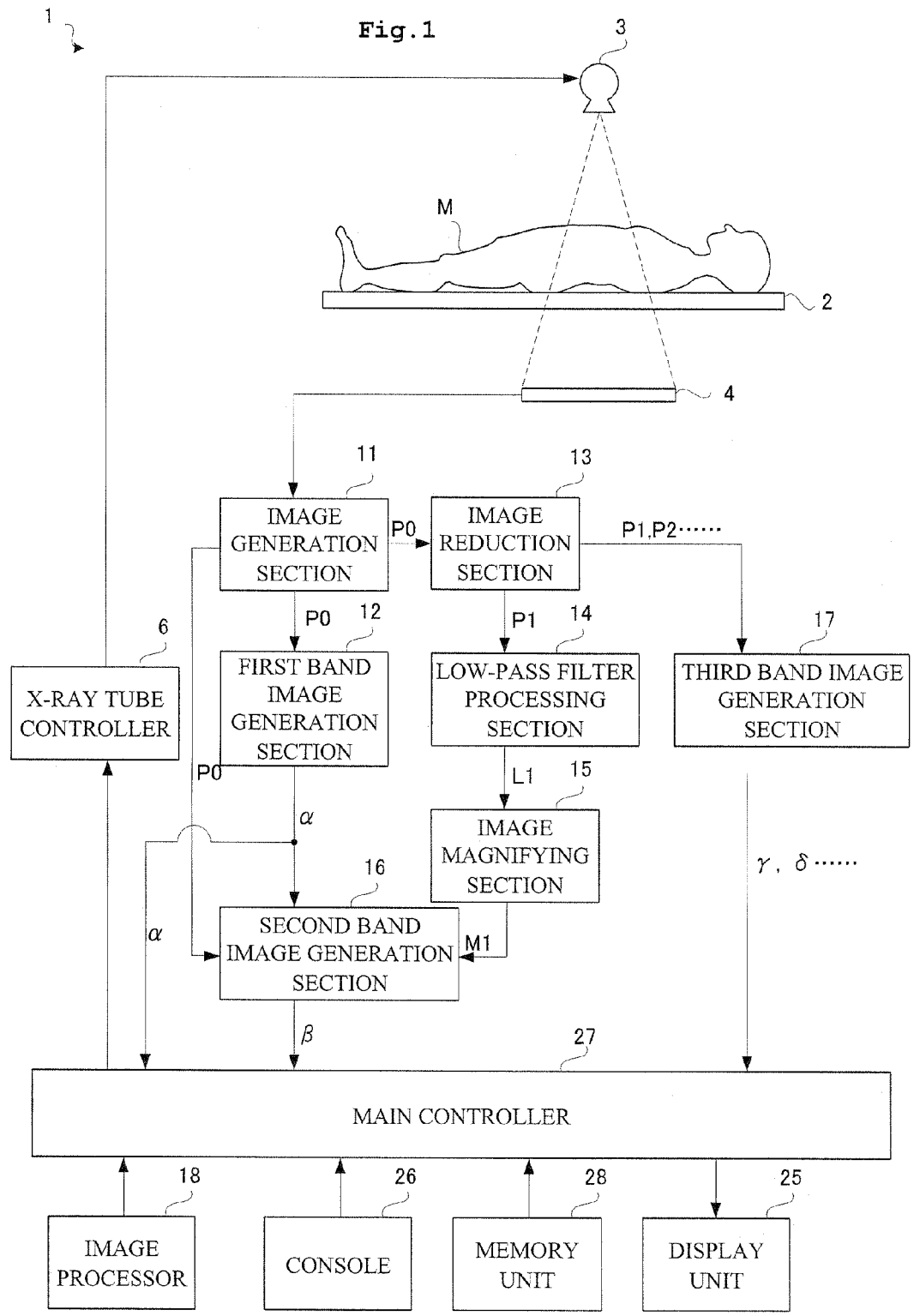
FIG. 1 is a functional block diagram illustrating a construction of X-ray apparatus according to Embodiment 1.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

An embodiment of this invention will be described hereinafter. X-rays in the embodiment correspond to radiation in this invention. An FPD is the abbreviation of a flat panel detector.

<Whole Configuration of X-Ray Apparatus>

Firstly, description will be given of a configuration of X-ray apparatus 1 according to Embodiment 1. As shown in FIG. 1, the X-ray apparatus 1 includes a top board 2 for supporting a subject M, an X-ray tube 3 above the top board 2 for emitting X-rays, and an FPD 4 below the top board 2 for detecting X-rays. The X-ray tube 3 corresponds to the radiation source in this invention. The FPD 4 corresponds to the radiation-detecting device in this invention.

An X-ray tube controller 6 is provided for controlling the X-ray tube 3 with a given tube current, a tube voltage, and a pulse width. The FPD 4 detects X-rays emitted from the X-ray tube 3 and transmitting through the subject M, and generates a detection signal. The detection signal is sent out to an image generation section 11, where a source image P0 is generated having a projected image of the subject M falling thereon. A display unit 25 is provided for displaying the projected image of the subject M outputted from the image generation section 11. The image generation section 11 corresponds to the image generation device in this invention.

The X-ray apparatus 1 according to Embodiment 1 includes a first band image generation section 12 for generating a first band image α from a source image P0; an image reduction section 13 for reducing the source image P0 to generate a reduction image P1; a low-pass filter processing section 14 for performing low-pass filter processing to the reduction image P1 to generate a low-pass image L1; an image magnifying section 15 for magnifying the low-pass image L1 to generate a magnified low-pass image M1; a second band image generation section 16 for generating a second band image based on the source image P0, the magnified low-pass image M1, and the first band image α, a third band image generation section 17 for generating a third band image γ based on the reduction image P1. Moreover, the X-ray apparatus 1 includes an image processor 18 for performing image processing to the source image P0 with the band images α, β, and γ. The third band image generation section 17 corresponds to the third band image generation device in this invention, and the second band image generation section 16 to the second band image generation device in this invention. The image processor 18 corresponds to the image processing device in this invention, and the image reduction section 13 to the image reduction device in this invention. The image magnifying section 15 corresponds to the image magnifying device in this invention, and the low-pass filter processing section 14 to the low-pass filter-processing device in this invention.

Figure 2:
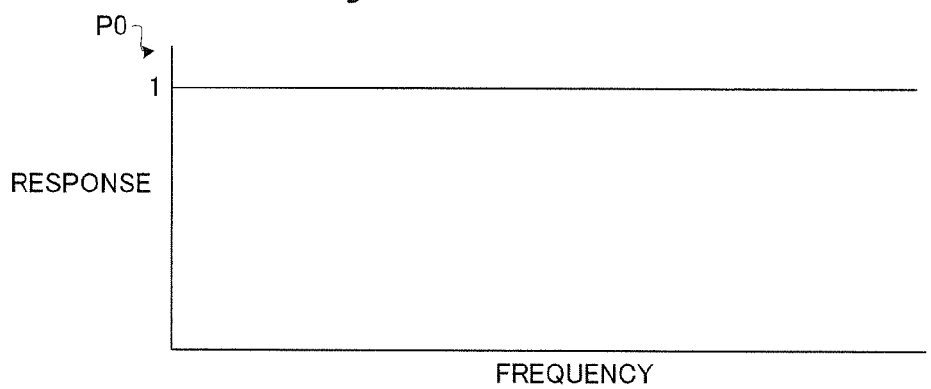
FIG. 2 is a schematic view illustrating frequency distribution of a source image according to Embodiment 1.
Figure 3:
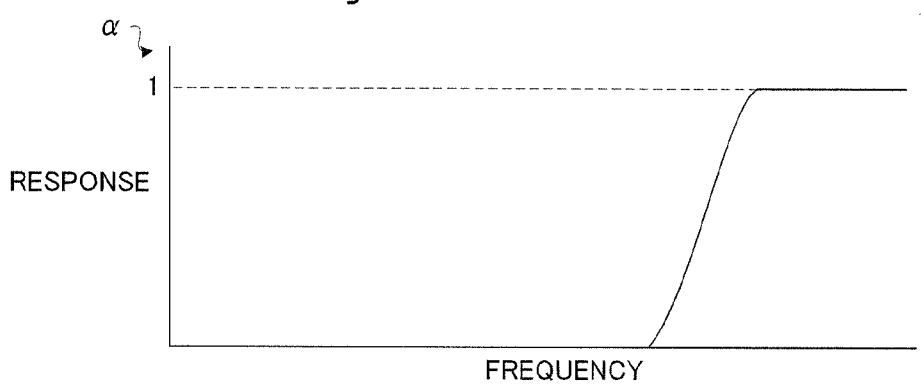
FIGS. 3 to 5 are schematic views each illustrating frequency distribution of a band image according to Embodiment 1.
Figure 4:
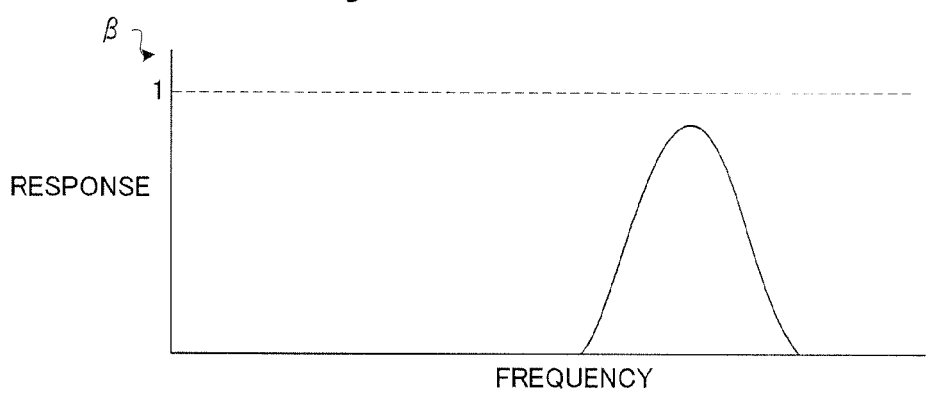
Figure 5:
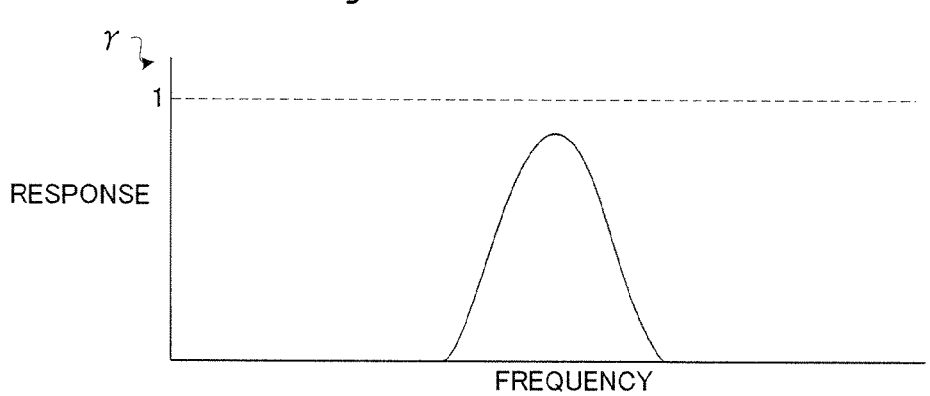

Next, description will be given of the band images α, β, and γ. FIG. 2 is the result of conducting frequency analysis of the source image P0. The source image P0 has wide frequency components from high frequencies to low frequencies. Here, for expediency of explanation, it is assumed that every frequency has a response of 1. FIG. 3 is the result of conducting frequency analysis of the first band image α. As illustrated in FIG. 3, the first band image α is an image having the frequency component extracted therefrom that is in a highest frequency region in the source image P0. FIG. 4 is the result of conducting frequency analysis of the second band image β. As illustrated in FIG. 4, the second band image β is an image having the frequency component extracted therefrom that is in a secondary highest frequency region in the source image P0. FIG. 5 is the result of conducting frequency analysis of the third band image γ. As illustrated in FIG. 5, the third band image γ is an image having the frequency component extracted therefrom that is in a thirdly highest frequency region in the source image P0. As above, the band images α, β, γ have the frequency components higher in this order that are derived from the source image P0.

A console 26 is provided for inputting operator's instructions such as start of emitting X-rays. Moreover, a main controller 27 is provided for performing an overall control of each controller. The main controller 27 has a CPU, and realizes the X-ray tube controller 6 and each section 11, 12, 13, 14, 15, 16, 17, 18 by executing various programs. The above sections may each be divided into arithmetic units that perform their functions. A memory unit 28 memorizes all parameters with respect to control of the X-ray apparatus 1 such as a parameter used for image processing, an intermediate image generated in connection with the image processing, and a table.

<Band Image Acquisition Method>

Figure 6:
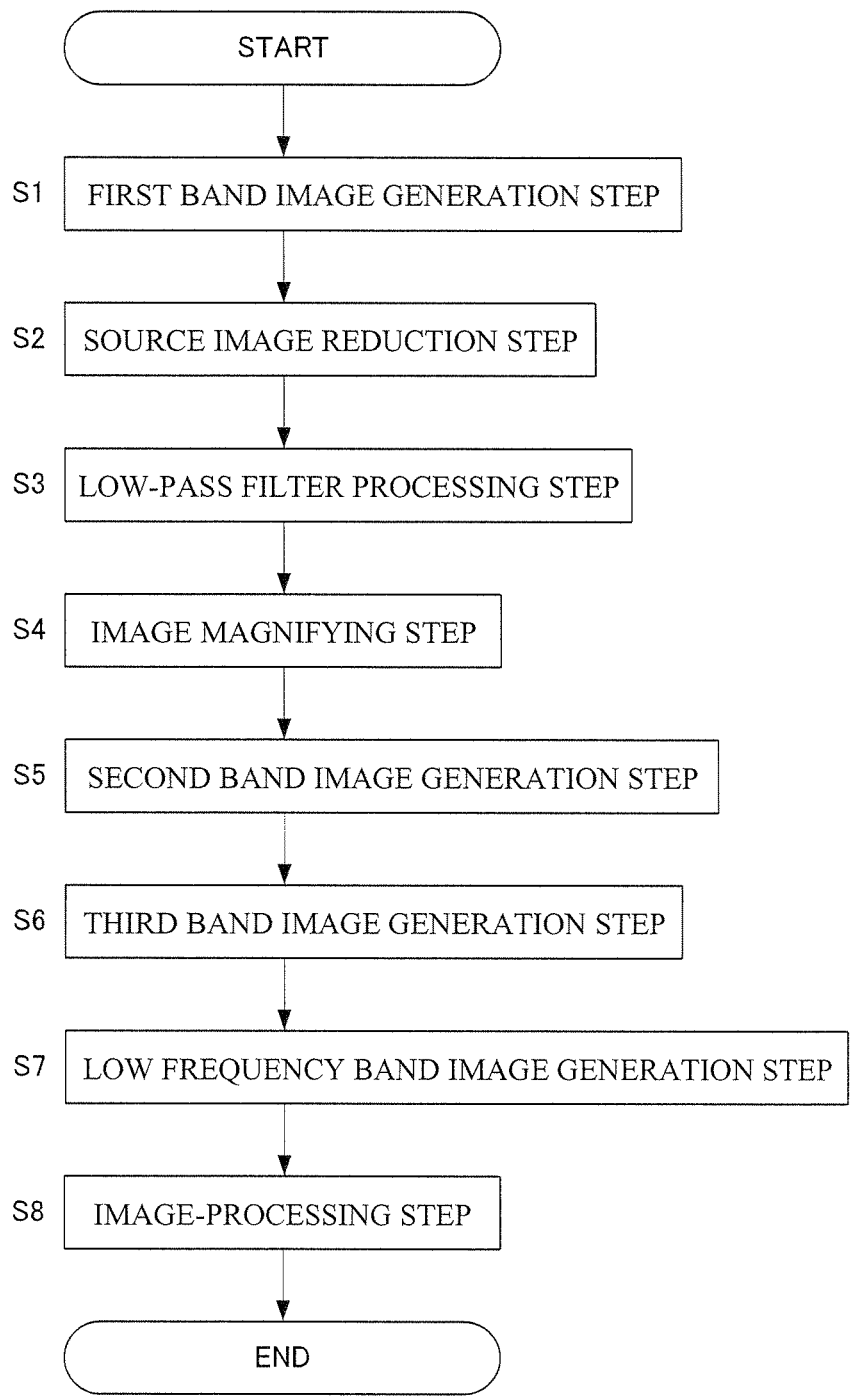
FIG. 6 is a flow chart illustrating operation of the X-ray apparatus according to Embodiment 1.

Next, description will be given of a method of acquiring the band images α, β, γ from the source image P0. In order to acquire the band images α, β, γ, a first band image α is firstly generated through high-pass filter processing to the source image P0 (a first band image generation step S1), and the reduction image P1 is generated through reduction of the source image P0 (a source image reduction step S2), as illustrated in FIG. 6. Thereafter, the reduction image P1 is subject to low-pass filter processing to generate a low-pass image L1 (a low-pass filter processing step S3), and the low-pass image L1 is magnified to generate a magnified low-pass image M1

(an image magnifying step S4.) Subsequently, a second band image β is generated based on the source image, the first band image α, and the magnified low-pass image M1 (a second band image generation step S5), and a third band image γ is generated through performing band-pass filter processing to the reduction image P1 (a third band image generation step S6.) Finally the band image of lower frequencies is generated (a low frequency band image generation step S7.) Here, the band images α, β, γ are acquired and used for performing a subsequent image-processing step S8. Each of these steps will be described in order.

<First Band Image Generation Step S1>

Figure 7:
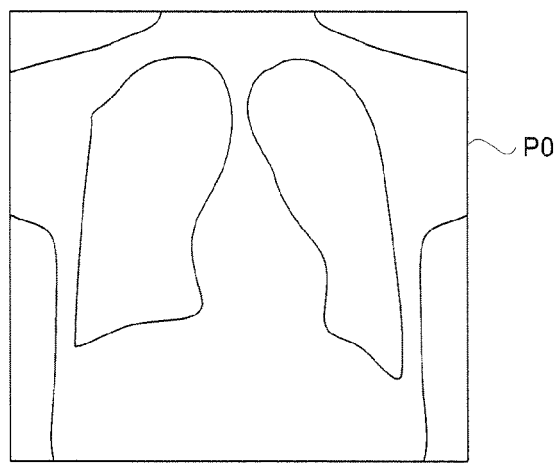
FIGS. 7 to 17 are schematic views each illustrating operations of the X-ray apparatus according to Embodiment 1.
Figure 8:
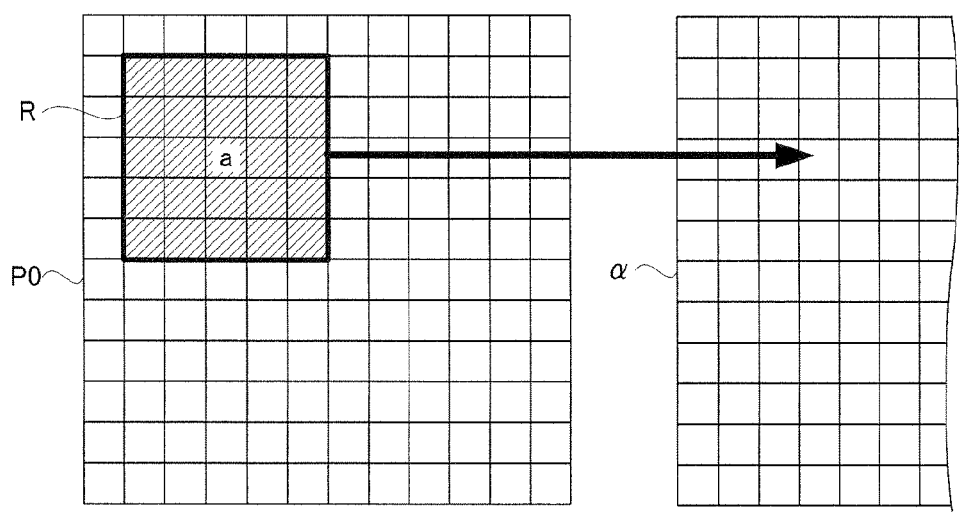

The source image P0 generated in the image generation section 11 (see FIG. 7) is sent to the first band image generation section 12. The first band image generation section 12 applies the matrix serving as a high-pass filter with respect to each of the pixels that form the source image P0. FIG. 8 illustrates a state where a pixel "a" forming the source image P0 is subject to high-pass filter processing. The first band image generation section 12 reads a matrix of 5×5, for example, for the high-pass filters from the memory unit 28, and applies the matrix to the pixel "a". Accordingly, as illustrated in FIG. 8, the matrix is applied to a pixel region R of five rows and five columns having the pixel "a" as a center thereof. Thereafter, the first band image generation section 12 places pixel data obtained through application of the matrix into a position corresponding to the pixel "a" in the first band image α. The first band image generation section 12 performs the same operation as above to all pixels, other than the pixel "a", that form the source image P0. The acquired pixel data is brought into correspondence with the source image P0, and is mapped in the first band image α on each occasion. The high-pass filter transmits only the high frequency components contained in the region R. Consequently, the first band image α becomes a rough image having the pixel data thereof varying finely. Here, it is assumed that a calculation cost be 1 necessary for generation of the first band image α. The first band image generation section 12 corresponds to the first band image generation device in this invention.

<Source Image Reduction Step S2>

Figure 9:
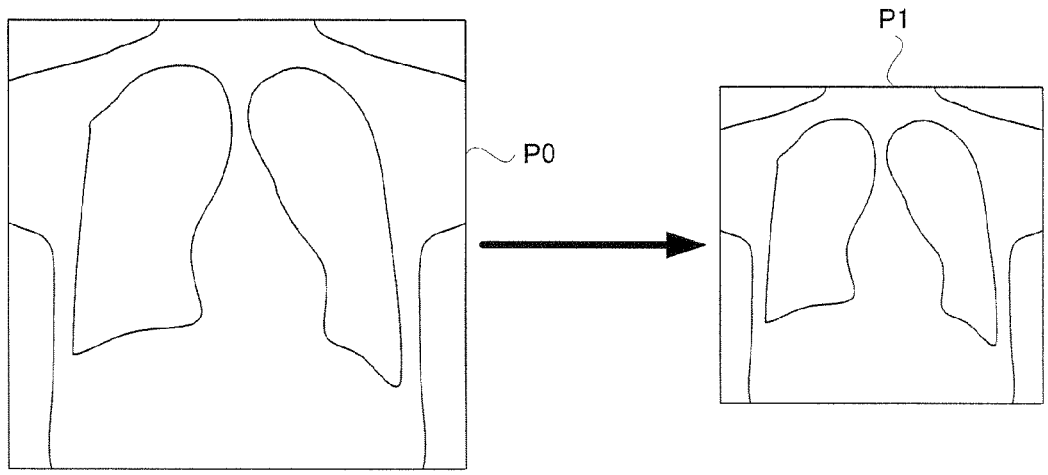

The source image P0 is also sent to the image reduction section 13. As illustrated in FIG. 9, the image reduction section 13 generates the reduction image P1 by reducing the source image P0 by half vertically and horizontally. Accordingly, the reduction image P1 is generated having ¼ times the area of the source image P0. The calculation cost for the image processing is extremely lower than that upon generation of the foregoing first band image α. That is because the image processing may be performed through merely bundling the pixel of 2×2. Consequently, the calculation cost for the reduction processing is almost 0. Every calculation cost for subsequent image processing by no use of the matrix is almost 0.

<Low-Pass Filter Processing Step S3>

The reduction image P1 is sent to the low-pass filter processing section 14. The low-pass filter processing section 14 reads the matrix for the low-pass filter of 5×5 that is equal in size to the matrix for the high-pass filters from the memory unit 28, and applies the matrix to each of the pixels forming the reduction image P1. The pixel data obtained through application of the matrix is brought into correspondence with the reduction image P1 and is mapped in the low-pass image L1, which situation is similar to the explanation using FIG. 8. Differences therebetween are the matrix to be used and the reduction image P1 to be processed having ¼ times the area of the source images P0. Accordingly, the calculation cost in this step is lower than 1, and specifically ¼. As noted above, the calculation cost may significantly be suppressed through reducing once the source image P0 and applying the low-pass filter by no use of the band-pass filter.

<Image Magnifying Step S4>

Figure 10:
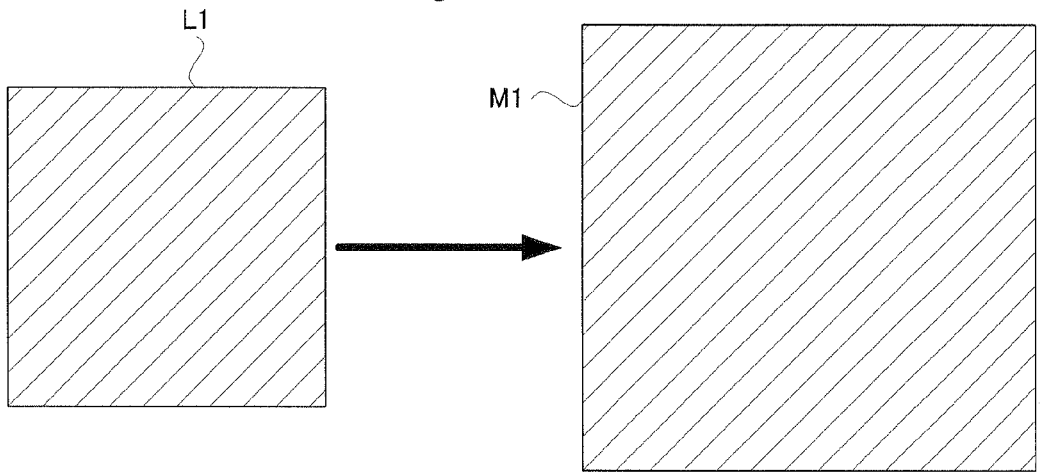

The low-pass image L1 is sent to the image magnifying section 15. As illustrated in FIG. 10, the image magnifying section 15 generates the magnified image M1 by magnifying the low-pass image L1 twice vertically and horizontally. That is, the magnified low-pass image M1 has the same size as the source image P0. Here, the calculation cost at this time is almost 0 comparing with that in the low-pass filter processing.

<The Second Band Image Generation Step S5>

The magnified low-pass image M1 is sent to the second band image generation section 16. The second band image generation section 16 also has the source image P0 and the first band image α already sent thereto. The second band image generation section 16 generates the second band image β through subtraction of the first band image α and the magnified low-pass image M1 from the source image P0.

Figure 11:
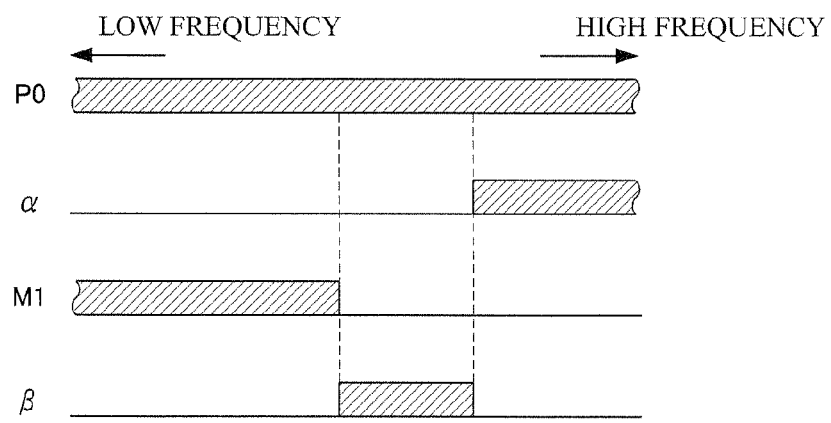

Description will be given of the second band image β. FIG. 11 is a schematic view illustrating a range of the frequency components contained in each image. As shown in FIG. 11, the source image P0 entirely has the frequency components. The first band image α contains only the highest frequency components, and thus has no low frequency component. On the other hand, the magnified low-pass image M1 is formed only of the low frequency components in the reduction image P1, and thus has no high frequency component. As illustrated in FIG. 11, the second band image β having the first band image α and the magnified low-pass image M1 subtracted from the source image P0 has frequency components among all frequency components of the source image P0 in a section between the lowest frequency of the first band image α and the highest frequency of the magnified low-pass image M1.

<The Third Band Image Generation Step S6>

The reduction image P1 is also sent to the third band image generation section 17. The third band image generation section 17 reads the matrix for the band-pass filter of 9×9 that is approximately twice the matrix for the low-pass filter from the memory unit 28, and applies the matrix to each of the pixels forming the reduction image P1. The pixel data obtained through application of the matrix is brought into correspondence with the reduction image P1, and is mapped in the third band image β, which situation is similar to the explanation using FIG. 8. Differences therebetween are various types of matrix to be used, the matrix having twice the length and width, and the reduction image P1 to be processed having ¼ times the area of the source images P0. Here, the band-pass filter has an approximately four times area of the low-pass filter. Accordingly, the calculation cost in this step with respect to every pixel should increase by approximately four times of that in the first band image generation step S1. The reduction image P1, however, has ¼ times the area of the source image P0. Finally, the calculation cost in this step is almost 1.

The third band image γ generated as above additionally has the frequency component of the source image P0 in the low frequency band rather than the second band image β.

<Low Frequency Band Image Generation Step S7>

The image reduction section 13 also generates the reduction image P2, other than the reduction image P1, that is obtained through reduction of the reduction image P1 by half vertically and horizontally. The reduction image P2 is sent to the third band image generation section 17 to generate a fourth band image δ. The calculation cost at this time is reduced by ¼ times of that in the third band image generation step S6, and therefore is approximately ¼. A reduction image P3 may be generated through further reducing the reduction image P2 by half vertically and horizontally for additional extraction of the low frequency component from the source image P0. The reduction image P3 may be sent to the third band image generation section 17. The calculation cost in the third band image generation section 17 with respect to the reduction image P3 is reduced by ¼ times of that with respect to the reduction image P2, and therefore is approximately 1/16.

A fourth band image δ generated as above additionally has the frequency component of the source image P0 extracted from the low frequency band rather than the third band image γ. In this way, the third band image generation section 17 may generate the band image of the low frequencies than the third band image γ. These band images may also be used for subsequent image processing. However, upon explanation of Embodiment 1, image processing is to be performed with the band images α, β, γ for simple explanation.

The calculation cost in Step S1 to Step S7 may be expressed by $1+¼+1+¼+1/16+\ldots$, and thus is approximately of 2.58. On the other hand, the calculation cost in the conventional art by the first method is approximately of 6.33, and that by the second method is approximately of 1.33.

The two or more band images generated in such way are memorized in the memory unit 28, and are used for various image processing performed in the image processor 18.

<Operation of Image Processor: Image-Processing Step S8>

The X-ray apparatus 1 according to Embodiment 1 may perform noise reduction processing, high frequency enhancement processing, and dynamic range compression processing to the source image P0 using the band images α, β, γ. Description will be given of a specific approach of each processing.

<Noise Reduction Processing>

Figure 12:
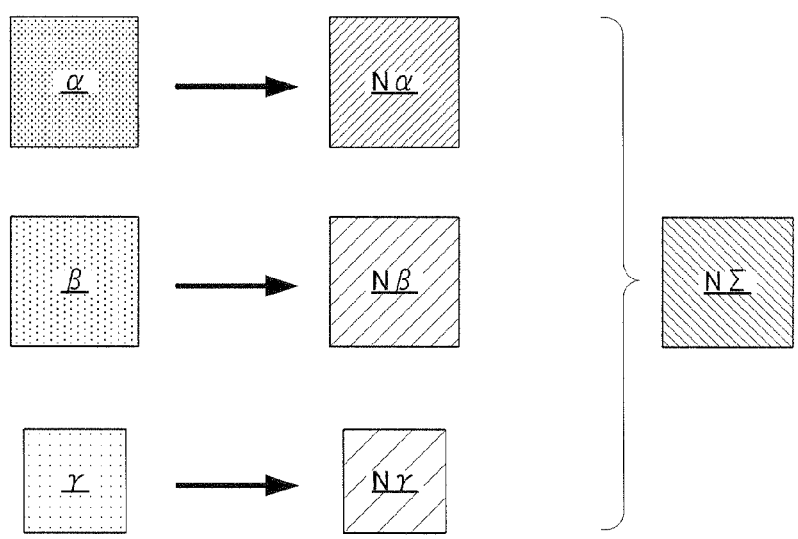

Firstly, description will be given of a specific method of noise reduction processing. As illustrated in FIG. 12, the image processor 18 performs given image processing to each band image α, β, γ, thereby generating a noise extracted image Nα, Nβ, Nγ with respect to the band image α, β, γ, respectively, having noise components in the band image α, β, γ extracted therefrom.

The image processor 18 adds the noise extracted images Nα, Nβ, Nγ while magnifying them as appropriate to generate an overall noise image NΣ having all noises in the source image P0 mapped therein. The image processor 18 has the source image P0 sent thereto, and subtracts the overall noise image NΣ from the source image P0. Accordingly, a noise removal image may be acquired having the noise components removed therefrom.

<High Frequency Enhancement Processing>

Next, description will be given of high frequency processing having enhanced high frequency components in the source image P0. Accordingly, fine portions in the source image P0 are observable in detail. In the X-ray apparatus 1 according to Embodiment 1, the band images α, β, γ are called up to the image processor 18 in order to perform high frequency enhancement processing to the source image P0. Thereafter, the image processor 18 converts pixel data forming the band images α, β, γ for generating a respective absolute value suppression image LUT.

Figure 13:
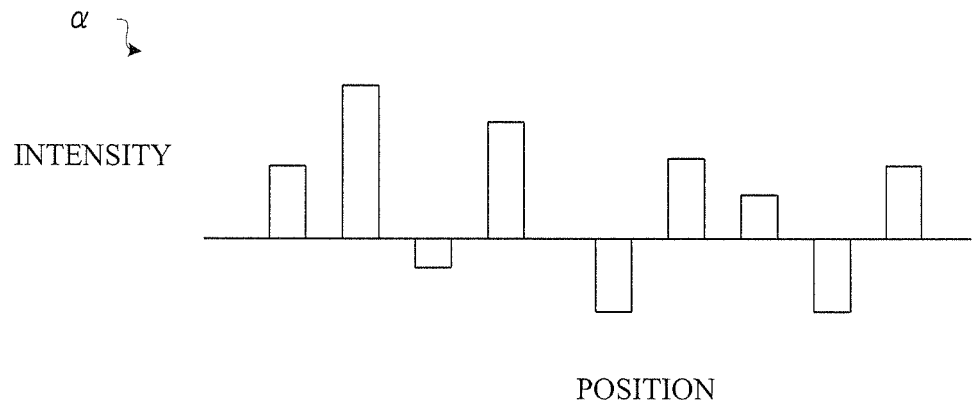

Description will be given in detail of generation of the absolute value suppression image LUT. Description has already been given of the band image having the pixel data mapping therein. The pixel data may be in a range from a positive value to a negative value. FIG. 13 illustrates a specific configuration of the first band image α. The pixel data forming the first band image α has a positive or negative value (intensity) depending on its position.

The image processor 18 reads a translation table for high frequency enhancement processing memorized in the memory unit 28, and translates the band images α, β, γ into the absolute value suppression images LUT(α), LUT(β), LUT(γ), respectively. This processing may suppress irregularities of the image appearing in the high frequency enhanced image finally acquired. For instance, suppose that the band images α, β, γ are used as they are with no absolute value suppression image LUT being generated. Then, when the image generated from the band images α, β, γ and the source image P0 are superimposed for generation of the high frequency enhanced image, a large positive or negative value of the band images α, β, γ is directly superimposed on the source image P0, which leads to reduced visibility of the high frequency enhanced image. Such phenomenon may occur as follows. That is, where the subject M having a metal piece embedded therein falls on the source image P0, a false image may readily appear in a boundary between the metal piece and the tissue of the subject M in the high frequency enhanced image. In the source image P0, the metal piece extremely differs from the tissue of the subject M in pixel data. In the band images α, β, γ, the extreme difference should be indicated as the frequency component. Specifically, an extremely large positive value or an extremely small negative value (i.e., a value with a large absolute value of the pixel data) is assigned to express the boundary. This may appear as a false image that borders the boundary upon generation of the high frequency enhanced image. Accordingly, the image processor 18 converts a large absolute value into a small absolute value of the pixel data that appears in the band images α, β, γ, thereby generating an absolute value suppression images (hereinafter, referred to as an LUT images.)

Figure 14:
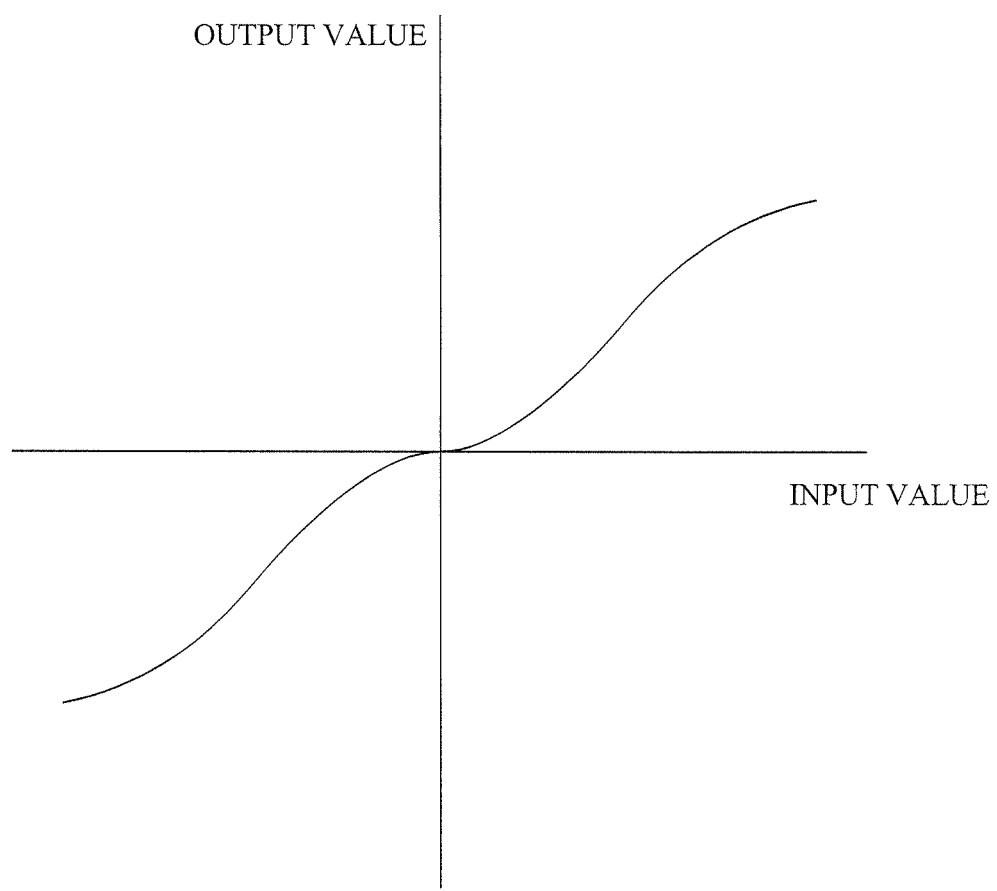

Description will be given of the translation table for the high frequency enhancement processing that the image processor 18 uses for the above translation. FIG. 14 is a graph associated with an input value and an output value of the translation table. The graph is a nonlinear profile symmetric about an origin point. The image processor 18 reads the pixel data forming the band images α, β, γ, and sets it as an input value. Then, the image processor 18 acquires an output value at this time from the translation table. The image processor 18 performs acquisition of the output value to every pixel data forming the first band image α, and maps the output values two-dimensionally, thereby acquiring a first LUT image Lα. Accordingly, the extremely large positive value and small negative value may be removed that are in the first band image α. The image processor 18 performs similar processing to the second band image β to generate a second LUT image Lβ. Likewise, the image processor 18 performs similar processing to the third band image γ to generate a third LUT image Lγ. This situation is illustrated on the left side of FIG. 15.

Subsequently, the image processor 18 performs weighting to the acquired LUT images L, and adds them up for generating a suppression combined image ΣLUT. The weighting may vary depending on purposes of the image processing. The third LUT image Lγ differs from the first LUT image Lα and the second LUT image Lβ in size of the image, and thus they cannot be added up as they are. Consequently, the image processor 18 once magnifies the third LUT image Lγ, and adds the magnified image to the first LUT image Lα and the second LUT image Lβ (see FIG. 15.) The suppression combined image LUT contains no low frequency component in the source image P0. That is because the frequency components lower than that extracted from the third band image γ are not summed to the suppression combined image ΣLUT.

Figure 15:
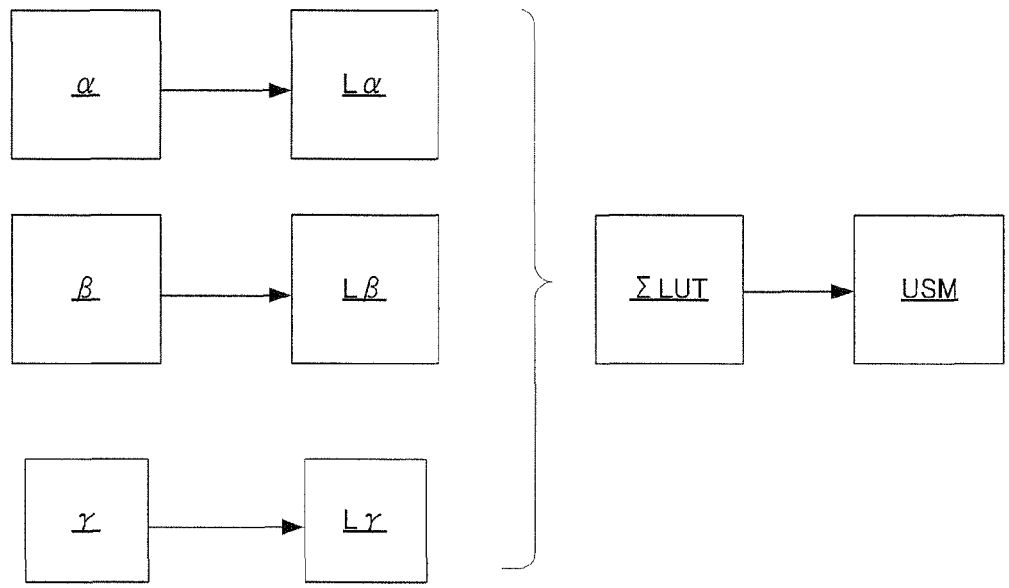

The image processor 18 performs a density conversion process to control the suppression combined image ΣLUT, and generates a density conversion image USM (see FIG. 15.) The density conversion image USM contains the high frequency components in the source image P0. Finally, the image processor 18 adds the source image P0 and the density conversion image USM to generate the high frequency enhanced image. Upon an actual addition of the source image P0 and the density conversion image USM, weighting is performed to both images, and thereafter the addition is performed. Adjusting the weighting may realize control of the high frequency enhancement processing.

<Dynamic Range Compression Processing>

Next, description will be given of dynamic range compression processing for controlling spread of the pixel data in the source image P0. Accordingly, a contrast in the source image P0 may be controlled. Where dynamic range compression processing is performed to the source image P0, the image processor 18 firstly adds the band images α, β, γ, while magnifying them as appropriate, thereby generating a compression combined image ΣBP. The compression combined image ΣBP has the lower frequency components removed from the source image P0, and is formed of the pixel data.

Figure 16:
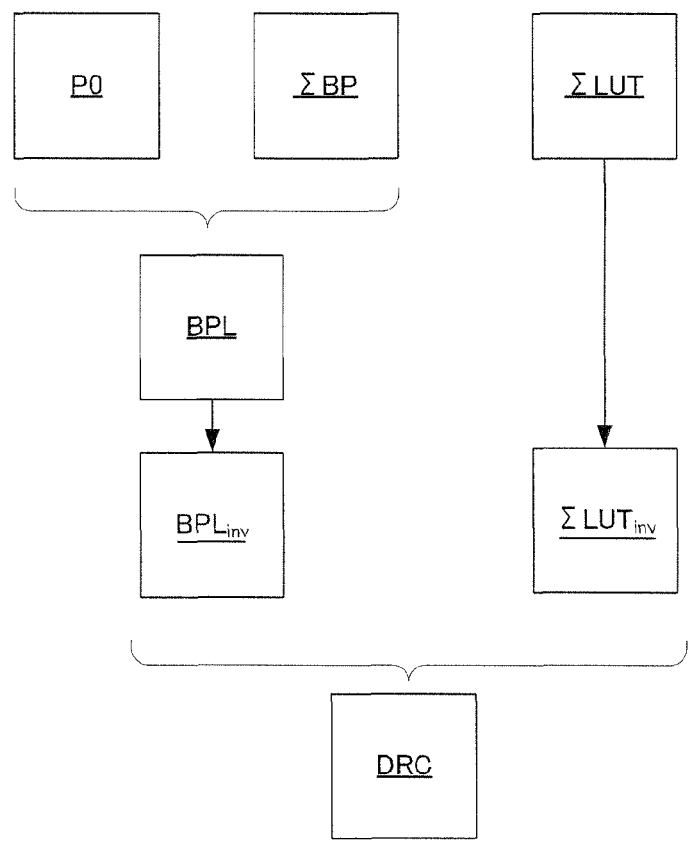

As illustrated in FIG. 16, the image processor 18 subtracts the compression combined image ΣBP from the source image P0 to acquire a low frequency component image BPL with only low frequency components. Subsequently, the image processor 18 reads a reversal table from the memory unit 28 for reversing the pixel data in the low frequency component image BPL, thereby generating a reverse low frequency component image $BPL_{inv}$. Here, the reversal table does not merely reverse the low frequency component image BPL linearly. Specifically, a little reversal is given to a density region to be observed, whereas greater one is given to the other regions as they are away from the observation region. Consequently, a dynamic range in the entire image is compressed while the contrast of the density region to be observed is maintained.

Figure 17:
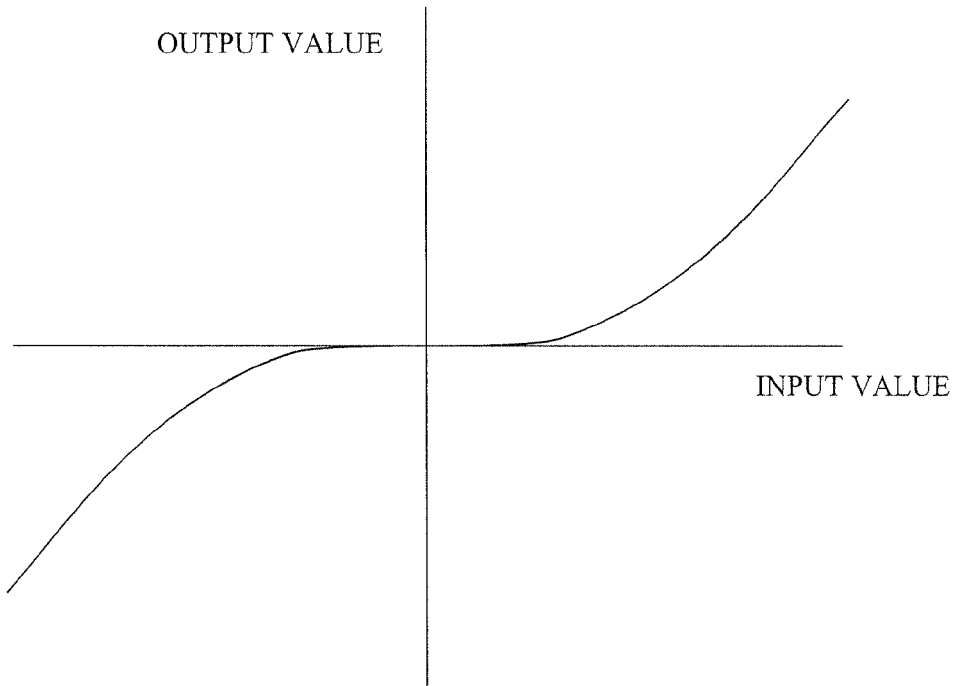
Figure 18:
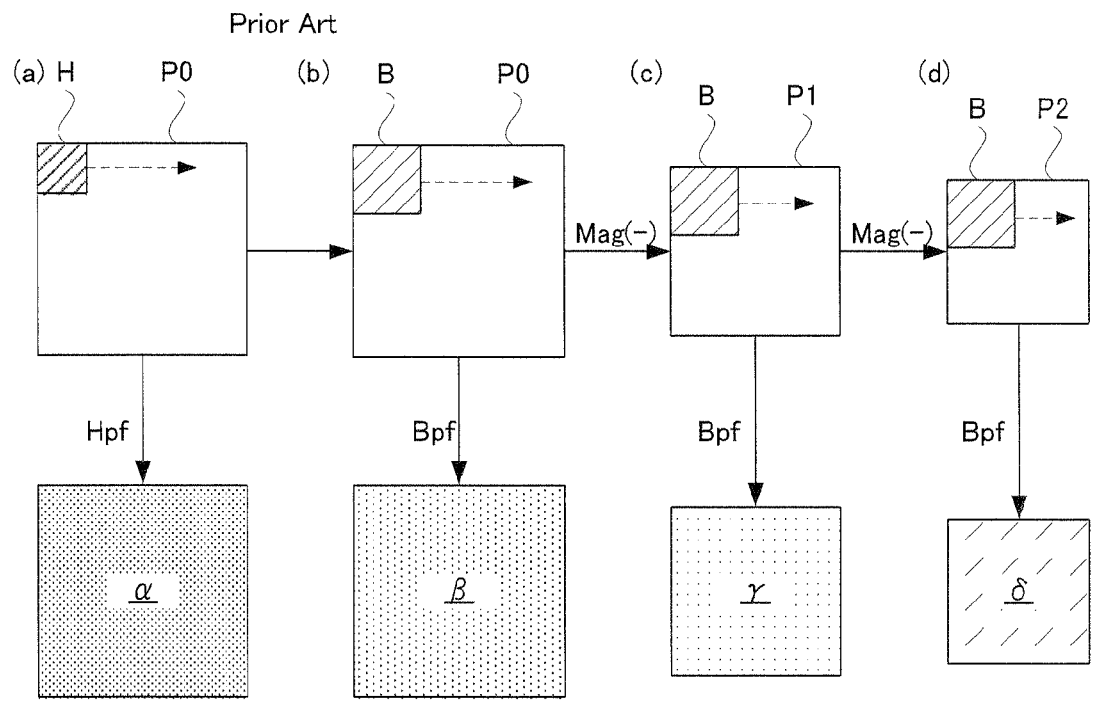

As described in the foregoing high frequency enhancement processing, the image processor 18 next generates a suppression combined image ΣLUT while performing weighting to the acquired LUT images L. The weighting may vary depending on purposes of the image processing. Here, the translation table used upon generation of the LUT images is for the dynamic range compression processing. As illustrated in FIG. 17, a graph expressing an input value and an output value of the translation table has a nonlinear profile symmetric about an origin point.

The image processor 18 reverses the pixel data in the suppression combined image ΣLUT, thereby generating a reverse suppression combined image $ΣLUT_{inv}$ (see FIG. 16.) Here, the reversal table is used different from that for generating the reverse low frequency component image $BPL_{inv}$. The low frequency components in the source image P0 are not contained in the suppression combined image ΣLUT.

Thereafter, the image processor 18 adds the reverse suppression combined image $ΣLUT_{inv}$ to the reverse low frequency component image $BPL_{inv}$. Here, addition is made such that larger weighting is performed to the reverse low frequency component image $BPL_{inv}$ than to the reverse suppression combined image $ΣLUT_{inv}$. Consequently, a reverse image DRC is generated (see FIG. 16.) The image processor 18 adds the source image P0 and the reverse image DRC to generate the dynamic range compression processing image.

The reason will be described for individual obtaining of the reverse low frequency component image $BPL_{inv}$ and the reverse suppression combined image $ΣLUT_{inv}$ upon generation of the dynamic range compression processing. The reverse low frequency component image $BPL_{inv}$ contains more low frequency components of the source image P0, whereas the reverse suppression combined image $ΣLUT_{inv}$ contains more high frequency components of the source image P0. Changing a table used for generating both combined images may control a balance of the dynamic range compression processing in the high frequency components and that in the low frequency components.

Description will be given of the reversal table for generating the reverse low frequency component image $BPL_{inv}$. The reversal table is a table having a relation between the input value expressing the pixel data that forms the low frequency component image BPL and the output value expressing the pixel data that forms the reverse low frequency component image $BPL_{inv}$. A portion of the table with the input value close to a reference value has an output value close to zero. When seen are the input values increasing in order from the reference value in the reversal table, the output value takes a negative value, and an absolute value thereof suddenly increases as the input value increases. On the other hand, when seen are the input values reduced in order from the reference value in the reversal table, the output value takes a positive value, and an absolute value thereof suddenly increases as the input value increases.

For simple explanation, it is assumed that the dynamic range compression processing image is generated through addition of the source image P0 and the reverse low frequency component image $BPL_{inv}$, and that the reverse suppression combined image $ΣLUT_{inv}$ is not under consideration. Here, supposing that every pixel data forming the reverse low frequency component image $BPL_{inv}$ is zero, the source image P0 and the dynamic range compression processing image are identical with each other. Moreover, supposing that the reverse low frequency component image $BPL_{inv}$ has a positive value on the right half thereof and a positive value on the left half thereof, the source image P0 has a bright portion on the right half and a dark portion on the left half.

The result of addition of the source image P0 and an actual reverse low frequency component image $BPL_{inv}$ is as under based on the above. That is, the pixel data of the reverse low frequency component image $BPL_{inv}$ has a value close to zero in the portion of the source image P0 having the pixel data close to the reference value. Consequently, no subtraction is performed. A portion of the source image P0 having a larger value than the reference value (bright portion) is dark, since the pixel data of the low frequency component image $BPL_{inv}$ has a negative value. On the other hand, a portion of the source image P0 having a smaller value than the reference value (dark portion) is bright, since the pixel data of the low frequency component image $BPL_{inv}$ has a positive value. In this way, the dynamic range in the source image P0 may be controlled. Upon actual addition of the source image P0 and the reverse low frequency component image $BPL_{inv}$, weighting is performed to both images, and thereafter the addition is performed. Adjusting the weighting may realize control of the dynamic range compression processing.

<Operation of X-Ray Apparatus>

Next, description will be given of operations of the X-ray apparatus 1. Firstly, the subject M is placed on the top board 2, and an operator instructs start of radiation irradiation via the console 26. Then, the X-ray tube 3 emits X-rays, and the FPD 4 detects X-rays transmitting through the subject M. Here, the source image P0 is generated. The band images α, β, γ are generated based on the source image P0.

The operator instructs execution of image processing via the console 26, and the image processor 18 performs noise reduction processing, high frequency enhancement processing, and dynamic range compression processing in accordance with the operator's instructions. A projected image of the subject M having image processing performed thereto is displayed on a display screen 25, and operations of the X-ray apparatus are completed.

According to the foregoing configuration as above, the source image P0 is once reduced and the low-pass filter is applied thereto. Thereafter, it is magnified for generation of the magnified low-pass image L1. The magnified low-pass image L1 is used for generation of the second band image β. Accordingly, the low-pass filter in a minimum dimension is applied to the image in a small size. Consequently, much time is not required for generating the second band image β. Moreover, according to the configuration of Embodiment 1, the band-pass filter is applied to the reduced image P1 for acquiring the third band image γ. That is, the configuration of Embodiment 1 has no configuration as adopted in the second method in the conventional art that performs redundant reduction/magnifying of the image. Accordingly, the third band image γ has a few artifacts. It takes most time for generating the second band image β. Consequently, according to Embodiment 1, the second band image has to be generated at a high-speed for enhancement of a processing speed for band image generation. Giving attention to this, the method required for necessarily performing magnifying of the image at a high speed is adopted only for generating the second band image β. Accordingly, the image processing method and the X-ray apparatus 1 may be provided having balanced generating time and image quality of the band image.

Moreover, in the foregoing configuration, the second band image generation section 16 generates the second band image β through application of the matrix for the low-pass filter to each pixel forming the reduction image P1. The third band image generation section 17 generates the third band image γ through application of the matrix for the band-pass filter to each pixel forming the reduction image P1. Here, the matrix for the low-pass filter in the second band image generation section 16 is smaller in size than that for the band-pass filter in the third band image generation section 17.

The larger the size of the image is, the larger the dimension of the matrix specifying the filter is, which leads to time-consuming image processing. The matrix specifying the band-pass filter is larger than that specifying the high-pass filter. Consequently, the band-pass filter requires more time where two filters are applied to the images in the same size. Here, according to the configuration of Embodiment 1, the images are reduced in advance and the low-pass filter is applied thereto instead of applying the band-pass filter to the source image. Accordingly, time for generating the second band image β may be suppressed. Here, the second band image β contains more low frequency components than the first band image α. The larger matrix is needed in order to extract the low frequency components. That is because the low frequency components spread broadly over the image rather than the high frequency components. Consequently, it is impossible to determine the matrix specifying the band-pass filter smaller than the high-pass filter. According to Embodiment 1, the second band image β may be generated at a high speed under such situation.

Moreover, as in the foregoing configuration, acquiring of the band images α, β, γ may realize estimation of the noise components superimposed in the source image P0, thereby positively removing the noise components from the source image P0.

Applying and adding up of the LUT images L generated from each band image α, β, γ may realize acquiring of the suppression combined image ΣLUT containing no low frequency component in the source image P0. When weighting is applied to this, the source image P0, and the combined image, and adds them up, the high frequency components in the source image P0 may be enhanced.

Here, the low frequency component image BPL containing the low frequency components in the source image P0 may be acquired through adding up each band image α, β, γ and subtracting thereof from the source image P0. Moreover, the suppression combined image LUT containing the high frequency components in the source image P0 may be acquired through adding up the LUT images L generated from each band image α, β, γ. The dynamic range compression processing is performed to the source image P0 through preparing these images individually and performing the reverse processing to the images, whereby the dynamic range compression processing may be controlled per each component through control of the methods of generating the low frequency component image BPL and the suppression combined image ΣLUT.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An image processing method for image processing a radiographic image with a subject falling thereon, comprising the steps of:
    generating a first band image through high-pass filter processing to a source image having an image of a subject falling thereon;
    generating a reduction image by reducing a size of the source image;
    performing low-pass filter processing to the reduction image to generate a low-pass image;
    magnifying the low-pass image to generate a magnified low-pass image;
    generating a second band image by subtracting the first band image and the magnified low-pass image from the source image;
    generating a third band image through performing of band-pass fitter processing to the reduction image; and
    performing image processing to the source image with each of the band images.

2. The image processing method according to claim 1, farther comprising the step of removing noise components superimposed in the source image through extraction of the noise components from each of the band images.

3. The image processing method according to claim 1, further comprising the steps of:
    acquiring a first combined image containing the high frequency components in the source image through weighting to each of the band images and adding them up; and
    performing high frequency enhancement processing to the source image by performing weighting to the combined image and the source image and adding them up.

4. The image processing method according to claim 2, further comprising the steps of:
    acquiring a first combined image containing the high frequency components in the source image through weighting to each of the band images and adding them up; and
    performing high frequency enhancement processing to the source image by performing weighting to the combined image and the source image and adding them up.

5. The image processing method according to claim 1, further comprising the steps of:
  acquiring the low frequency component image containing low frequency components in the source image;
  acquiring a second combined image containing high frequency components in the source image through weighting to each of the band images and adding them up;
  reversing pixel data nonlinearly that form the combined image and the low frequency component image, respectively, to generate a reverse image; and
  performing dynamic range compression processing to the source image through weighting to the reverse image and the source image and adding them up.

6. The image processing method according to claim 2, further comprising the steps of:
  acquiring the low frequency component image containing low frequency components in the source image;
  acquiring a second combined image containing high frequency components in the source image through weighting to each of the band images and adding them up;
  reversing pixel data nonlinearly that form the combined image and the low frequency component image, respectively, to generate a reverse image; and
  performing dynamic range compression processing to the source image through weighting to the reverse image and the source image and adding them up.

7. The image processing method according to claim 3, further comprising the steps of:
  acquiring the low frequency component image containing low frequency components in the source image;
  acquiring a second combined image containing high frequency components in the source image through weighting to each of the band images and adding them up;
  reversing pixel data nonlinearly that form the combined image and the low frequency component image, respectively, to generate a reverse image; and
  performing dynamic range compression processing to the source image through weighting to the reverse image and the source image and adding them up.

8. The image processing method according to claim 4, farther comprising the steps of:
  acquiring the low frequency component image containing low frequency components in the source image;
  acquiring a second combined image containing high frequency components in the source image through weighting to each of the hand images and adding them up;
  reversing pixel data nonlinearly that form the combined image and the low frequency component image, respectively, to generate a reverse image; and
  performing dynamic range compression processing to the source image through weighting to the reverse image and the source image and adding them up.

9. Radiographic apparatus for image processing a radiographic image with a subject falling thereon, comprising:
  a radiation source for emitting radiation;
  a radiation detecting device for detecting radiation;
  an image generation device for generating a source image having an image of a subject falling thereon in accordance with a detection signal outputted from the radiation detecting device;
  a first band image generation device for generating a first band image through high-pass filter processing to the source image;
  a source image reduction device for generating a reduction image by reducing a size of the source image;
  a low-pass filter processing device for performing low-pass filter processing to the reduction image to generate a low-pass image;
  an image magnifying device for magnifying the low-pass image to generate an magnified low-pass image;
  a second band image generation device for generating a second band image by subtracting the first band image and the magnified low-pass image from the source image:
  a third band image generation device for generating a third band image through performing of band-pass filter processing to the reduction image; and
  an image-processing device for performing image processing to the source image with each band image.

10. The radiographic apparatus according, to claim 9, wherein
  the image processing device removes noise components superimposed in the source image through extraction of the noise components from each of the band images.

11. The radiographic apparatus according to claim 9, wherein
  the image processing device acquires a combined image containing the high frequency components in the source image through weighting to each of the band images and adding it up, and performs high frequency enhancement processing to the source image by applying weighting to the combined image and the source image and adding them up.

12. The radiographic apparatus according, to claim 10, wherein
  the image processing device acquires a combined image containing the high frequency components in the source image through weighting to each of the band images and adding it up; and
  performs high frequency enhancement processing to the source image by applying weighting to the combined image and the source image and adding them up.

13. The radiographic apparatus according to claim 9, wherein
  the image processing device acquires the low frequency component image containing the low frequency components in the source image; acquires a combined image containing high frequency components in the source image through weighting to each of the band images and adding it up; reverses pixel data nonlinearly that form the combined image and the low frequency component image, respectively, to generate a reverse image; and performs dynamic range compression processing to the source image through weighting to the reverse image and the source image and adding thereof.

14. The radiographic apparatus according to claim 10, wherein
  the image processing device acquires the low frequency component image containing the low frequency components in the source image; acquires a combined image containing high frequency components in the source image through weighting to each of the band images and adding it up; reverses pixel data nonlinearly that form the combined image and the low frequency component image, respectively, to generate a reverse image; and performs dynamic range compression processing to the source image through weighting, to the reverse image and the source image and adding thereof.

15. The radiographic apparatus according to claim 11, wherein
  the image processing device acquires the low frequency component image containing the low frequency components in the source image; acquires a combined image containing high frequency components in the source image through weighting to each of the band images and adding it up; reverses pixel data nonlinearly that form the combined image and the low frequency component image, respectively, to generate a reverse image; and performs dynamic range compression processing to the source image through weighting to the reverse image and the source image and adding thereof.

16. The radiographic apparatus according to claim 12, wherein the image processing device acquires the low frequency component image containing the low frequency components in the source image; acquires a combined image containing high frequency components in the source image through weighting to each of the band images and adding it up; reverses pixel data nonlinearly that form the combined image and the low frequency component image, respectively, to generate a reverse image: and performs dynamic range compression processing to the source image through weighting to the reverse image and the source image and adding thereof.

* * * * *